(12) United States Patent
Stambuli

(10) Patent No.: US 8,022,227 B2
(45) Date of Patent: Sep. 20, 2011

(54) METHOD OF SYNTHESIZING 1H-INDAZOLE COMPOUNDS

(75) Inventor: James P. Stambuli, Dublin, OH (US)

(73) Assignee: The Ohio State University, Columbus, OH (US)

( * ) Notice: Subject to any disclaimer, the term of this patent is extended or adjusted under 35 U.S.C. 154(b) by 271 days.

(21) Appl. No.: 12/548,942

(22) Filed: Aug. 27, 2009

(65) Prior Publication Data

US 2010/0056800 A1   Mar. 4, 2010

Related U.S. Application Data

(60) Provisional application No. 61/092,085, filed on Aug. 27, 2008.

(51) Int. Cl.
    *C07D 231/56*   (2006.01)

(52) U.S. Cl. .................................................. 548/361.1

(58) Field of Classification Search .................. None
    See application file for complete search history.

(56) References Cited

U.S. PATENT DOCUMENTS 7,339,066 B1   3/2008   Parker et al.

OTHER PUBLICATIONS

Jin et al., "An Efficient, Facile, and General Synthesis of 1H-Indazoles by 1,3-Dipolar Cycloaddition of Arynes with Diazomethane Derivatives", Agnew. Chem. Int. Ed., 46, pp. 3323-3325, Mar. 27, 2007.

Counceller et al., "A Practical, Metal-Free Synthesis of 1H-Indazoles", American Chemical Society, Organic Letters, vol. 10, No. 5, pp. 1021-1023, Jan. 9, 2008.

Lukin et al., "New Practical Synthesis of Indazoles via Condensation of o-Fluorobenzaldehydes and Their O-Methyloximes with Hydrazine", J. Org. Chem., 71, pp. 8166-8172, Jul. 3, 2006.

Watson et al., "Process Improvements for the Preparation of Kilo Quantities of a Series of Isoindoline Compounds", Organic Process Research & Development, 7, pp. 571-532 (2003).

Vina et al., "Regioselective Synthesis of 1-Alkyl—or 1-Aryl-1H-indazoles via Copper Catalyzed Cyclizations of 2-Haloarylcarbonylic Compounds", American Chemical Society, Organic Letters, Vo. 9, No. 3, pp. 525-528 (2007).

O'Dell et al., "Synthesis of 1H-Indazoles by Reductive Cyclization of o-Nitro-Ketoximes", Hetercycles, vol. 63, No. 2, (2004).

Inamoto et al., "Synthesis of 3-substituted indazoles and benzoisoxazoles via Pd-catalyzed cyclization reactions: application to the synthesis of nigellicine", ScienceDirect, pp. 2695-2711, Jan. 9, 2007.

Zhu et al., "Syntheses of Potent, Selective, and Orally Bioavailable Indazole-Pyridine Series of Protein Kinase B/Akt Inhibitors with Reduced Hypotension", J. Med. Chem, 50, pp. 2990-3003, Jan. 25, 2007.

Caron et al., "A Versatile and Efficient Synthesis of Substituted 1H-Indazoles", Synthesis, No. 4, pp. 588-592, (1999).

*Primary Examiner* — Kamal Saeed
(74) *Attorney, Agent, or Firm* — Dinsmore & Shohl LLP

(57) ABSTRACT

A method is provided for synthesizing 1H-indazole compounds in which aromatic carbonyl compounds are reacted with a nitrogen source to form oximes which are then converted to 1H-indazoles.

16 Claims, No Drawings

METHOD OF SYNTHESIZING 1H-INDAZOLE COMPOUNDS

CROSS-REFERENCE TO RELATED APPLICATIONS

This application claims the benefit of U.S. Provisional Application No. 61/092,085, filed Aug. 27, 2008, entitled METHOD OF SYNTHESIZING 1H-INDAZOLES. The entire contents of said application is hereby incorporated by reference.

BACKGROUND OF THE INVENTION

The present invention relates to a method of synthesizing 1H-indazole compounds, and more particularly, to a method which utilizes mild operating conditions to react aromatic carbonyl compounds with a nitrogen source to form oximes which are converted to 1H-indazoles.

Indazoles, and particularly, 1H-indazoles, form the core structures of many diverse pharmaceutical products. For example, 1H-indazoles may be used in anti-cancer, fertility, arthritic, anti-inflammatory and contraceptive pharmaceutical products. In addition, 1H-indazoles have demonstrated activity as HIV protease inhibitors, and 5-HT$_3$ antagonists. As a result, it has become increasingly desirable to be able to develop safe and efficient methods of producing indazoles.

1H-indazole compounds are typically synthesized under harsh conditions which include the use of strong acids, strong bases, or high temperatures. More recent methods have involved the use of metals, which are undesirable, or have produced indazoles having limited product scope.

Other recent approaches to the synthesis of 1H-indazole compounds are shown in scheme 1 below and include the addition of hydrazine to fluorobenzaldehydes.

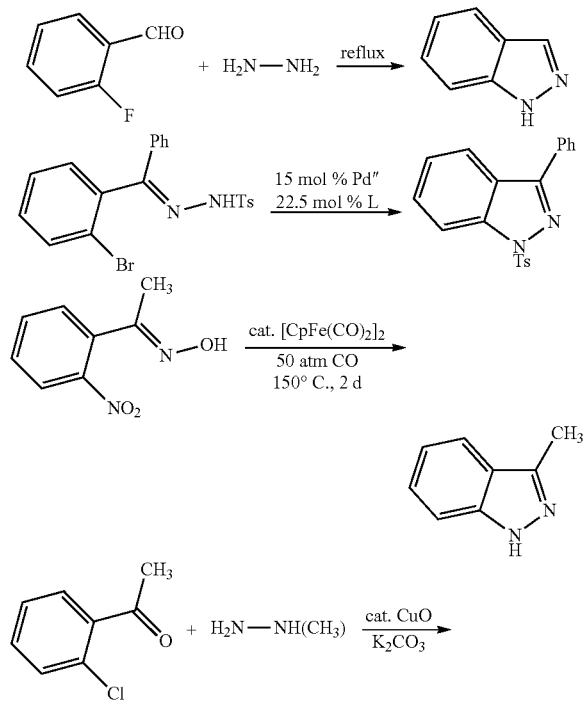

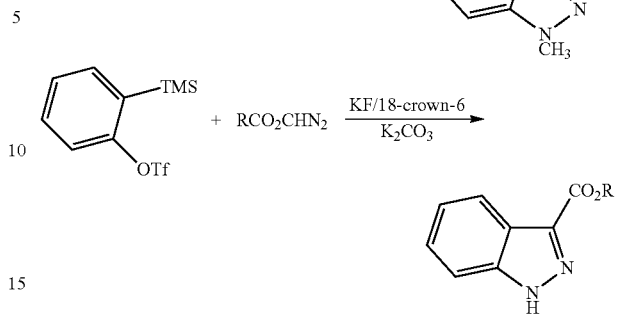

However, the scope of this reaction is limited to the use of fluorobenzaldehydes and does not allow substitution at the 3-position.

The palladium-catalyzed synthesis of indazoles from hydrazones requires a high catalyst loading of palladium and provides only a tosyl-protected type of indazole. The Nichols method may also be used to make indazoles, but requires long reaction times, high temperatures and CO pressure, and an iron catalyst. The CuO catalyzed method provides only methyl-protected type indazoles, and the yields are low.

More recently, the synthesis of indazoles has been achieved via 1,3-dipolar cycloaddition reactions of arynes and diazomethane derivatives. See Jin et al., "An Efficient, Facile, and General Synthesis of 1H-Indazoles by 1,3-dipolar Cycloaddition of Arynes with Diazomethane Derivatives, *Angew. Chem. Int. Ed.*, 2007, 46, 3323-3325.

However, the limited substrate scope, and in some instances, impractical conditions used in the current methods, demonstrates the need for a more general method of synthesizing indazoles.

Accordingly, there is still a need in the art for a method of synthesizing 1H-indazole compounds for use in pharmaceutical and other applications.

SUMMARY OF THE INVENTION

Embodiments of the invention meet that need by providing a method of making 1H-indazole compounds utilizing mild operating conditions which allow a broad reaction scope.

According to one aspect of the invention, a method is provided for making 1H-indazole compounds which comprises providing an aromatic carbonyl compound having the formula

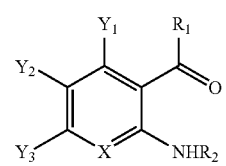

where $R_1$ is H, an alkyl, an aryl, or heteroaryl; $R_2$ is H, an alkyl, aryl, allyl, alkylsulfonyl, or arylsulfonyl; X is N or $CY_4$; $Y_1$, $Y_2$, $Y_3$, and $Y_4$ independently represent H, an alkyl, aryl, alkoxy or a halogen; and wherein optionally one or more of $Y_1$ and $Y_2$, $Y_2$ and $Y_3$, or $Y_3$ and $Y_4$ can be connected to form at least one ring. The at least one ring may optionally be substituted with one or more groups selected from alkyl, aryl, alkoxy, and halogen.

The aromatic carbonyl compound is reacted with a nitrogen containing base to form an oxime reaction product having the formula

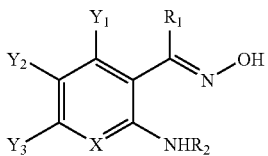

with $R_1$, $R_2$, X, $Y_1$, $Y_2$, and $Y_3$ as defined above, and an activating agent is added in the presence of a weak base to the oxime reaction product such that the oxime reaction product is converted to a 1H-indazole compound having the formula

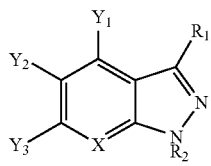

The oxime product is converted at a temperature between about 0° C. and about 23° C.

By "weak base," it is meant a chemical base compound that does not fully dissociate. A preferred weak base for use in the method is triethylamine ($NEt_3$).

The aromatic carbonyl compound is preferably selected from o-aminobenzaldehydes and o-aminoketones. The nitrogen containing base is preferably hydroxylamine. The activating agent is selected from methanesulfonylchloride (MsCl), tosyl chloride (TsCl), methylchloroformate, and pentafluorobenzoyl chloride.

The reaction scheme for one embodiment of the synthesis is shown below in formula (1):

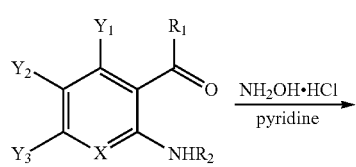

(1)

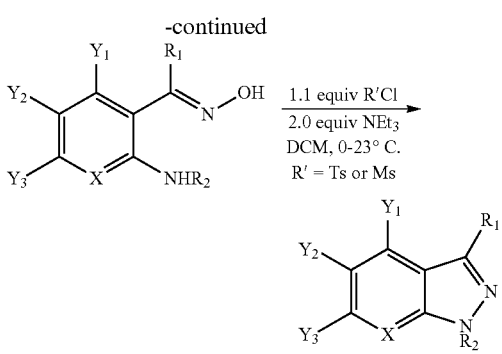

where $R_1$ is H, an alkyl, an aryl, or heteroaryl; $R_2$ is H, an alkyl, aryl, allyl, alkylsulfonyl, or arylsulfonyl; X is N or $CY_4$; $Y_1$, $Y_2$, $Y_3$, and $Y_4$ independently represent H, an alkyl, aryl, alkoxy or halogen; and wherein optionally one or more of $Y_1$ and $Y_2$, $Y_2$ and $Y_3$, or $Y_3$ and $Y_4$ can be connected to form at least one ring. The at least one ring may optionally be substituted with one or more R groups.

Accordingly, it is a feature of the present invention to provide a method of synthesizing 1H-indazoles utilizing mild operating conditions. Other features and advantages of the invention will be apparent from the following description and the appended claims.

DETAILED DESCRIPTION

The method of the present invention offers many advantages over prior art methods of synthesizing 1H-indazole compounds as it uses metal-free, mild operating conditions (i.e., reaction occurs at ambient temperatures in the absence of strong acids or bases) and allows the production of a wide variety of 1H-indazole compounds as the method tolerates different functional groups.

The method can be used to produce a wide variety of 1H-indazoles. Non-limiting examples of 1H-indazoles produced by the method are shown in Table 1 below, where $R_1$, and $R_2$ are as previously defined, and each R is independently selected from H, alkyl, aryl, alkoxy, or halogen.

TABLE 1

Synthesis of 1H-Indazoles

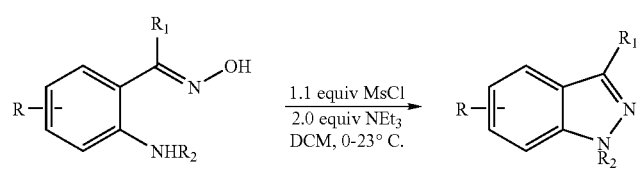

| Entry | Oxime | 1H-Indazole | Yield (%) |
|---|---|---|---|
| 1 | | | 77 |

TABLE 1-continued
Synthesis of 1H-Indazoles
| Entry | Oxime | 1H-Indazole | Yield (%) |
|---|---|---|---|
| 2 | | | 81 |
| 3 | | | 86 |
| 4 | | | 75 R = OCH$_3$ |
| 5 | | | 86 |
| 6 | | | 38 |
| 7 | | | 82 |
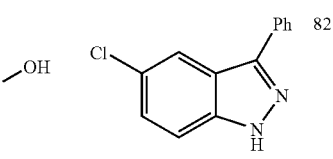

TABLE 1-continued

Synthesis of 1H-Indazoles

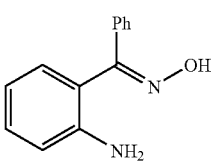

| Entry | Oxime | 1H-Indazole | Yield (%) |
|---|---|---|---|
| 8 | 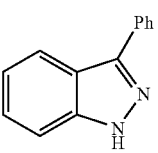 Ph | 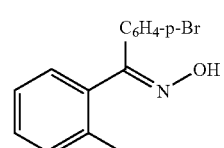 Ph | 84 |
| 9 | 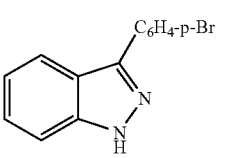 $C_6H_4$-p-Br | 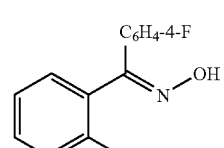 $C_6H_4$-p-Br | 81 |
| 10 | 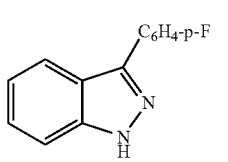 $C_6H_4$-4-F | 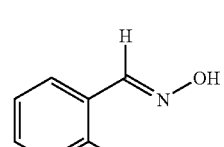 $C_6H_4$-p-F | 86 |
| 11 | 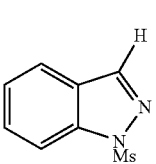 H | H, Ms | 52[a] |

[a] 2 equiv of MsCl used at −20° C.

As can be seen, 1H-indazoles containing substitution on the phenyl ring or at the 3-position are tolerated. The substitution may also include acid-sensitive groups such, for example, furans (see entry 5).

In addition, the method can be used to synthesize 1H-indazoles with N-substituted compounds as shown below in Table 2. In one embodiment, the use of pentafluorobenzoyl chloride may be used in place of methanesulfonyl chloride.

TABLE 2

Synthesis of N-Substituted 1H-Indazoles

Reaction: Oxime with NHR₂ ortho substituent → 1H-Indazole, conditions: 1.1 equiv MsCl, 2.0 equiv NEt₃, DCM, 0-23° C.

| Entry | Oxime | 1H-Indazole | Yield (%) |
|---|---|---|---|
| 1 | R₁ = CH₃; NH-CH₃ | 3-CH₃, 1-CH₃ indazole | 87 |
| 2 | R₁ = CH₃; NH-allyl | 3-CH₃, 1-allyl indazole | 70 |
| 3 | R₁ = CH₃; NH-Ts | 3-CH₃, 1-Ts indazole | 26 |
| 4 | R₁ = CH₃; NH-(4-methylphenyl) | 3-CH₃, 1-(4-methylphenyl) indazole | 47[a] |

[a] Pentafluorobenozyl chloride is used in place of methanesulfonyl chloride

The method also provides an alternative approach to the synthesis of N-aryl 1H-indazoles as shown in Table 3.

TABLE 3

Synthesis of N-Aryl 1H-Indazoles

Reaction: Oxime with NHR₂ ortho substituent → 1H-Indazole, conditions: 1.1 equiv MsCl, 2.0 equiv NEt₃, DCM, 0-23° C.

| Entry | Oxime | 1H-Indazole | Yield (%) |
|---|---|---|---|
| 1 | R₁ = CH₃; NH-(4-nitrophenyl) | 3-CH₃, 1-(4-nitrophenyl) indazole | 61 |
| 2 | R₁ = CH₃; NH-(4-trifluoromethylphenyl) | 3-CH₃, 1-(4-trifluoromethylphenyl) indazole | 26 |
| 3 | R₁ = CH₃; NH-(4-fluorophenyl) | 3-CH₃, 1-(4-fluorophenyl) indazole | 34 |

In another embodiment, the synthesis of N-aryl 1H-indazoles is expanded by replacing triethylamine (NEt₃) with 2-aminopyridine as shown in Table 4 below. Except as otherwise noted, groups $R_1$ and $R_2$ are as previously defined.

TABLE 4
Synthesis of N-Arylindazoles
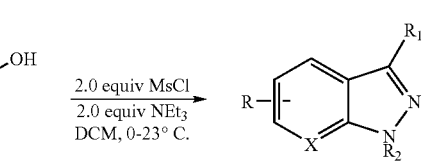
base =
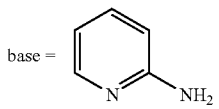
| Entry | Oxime | Indazole | Yield (%) |
|---|---|---|---|
| 1 | | | 87 |
| 2 | | | 72 |
| 3 | | | 90 |
| 4 | | | 86[a] |
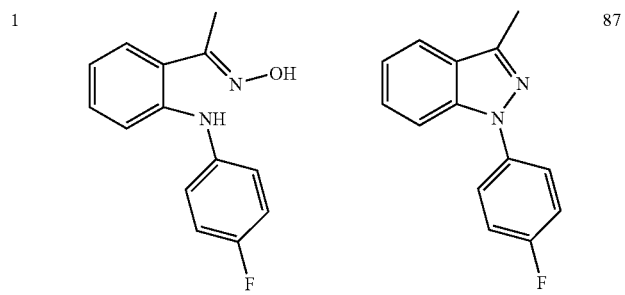
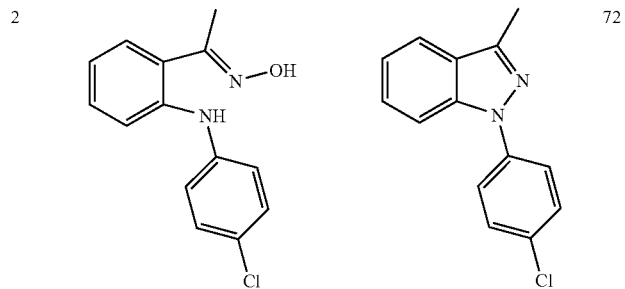
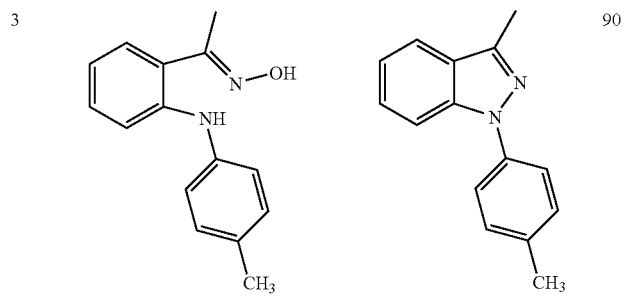
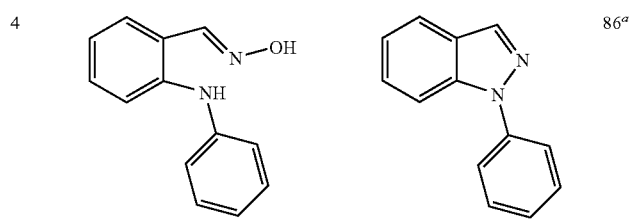

TABLE 4-continued
Synthesis of N-Aryindazoles
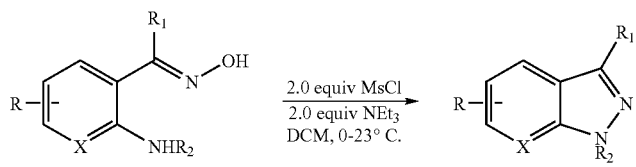
base = 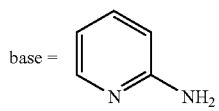
| Entry | Oxime | Indazole | Yield (%) |
|---|---|---|---|
| 5 | | | 94 |
| 6 | | | $R_2$ = F, 66<br>$R_2$ = Cl, 69<br>$R_2$ = OCH$_3$, 82 |
| 7 | | | 82 |
| 8 | | | 81 |

TABLE 4-continued

Synthesis of N-Arylindazoles

| Entry | Oxime | Indazole | Yield (%) |
|---|---|---|---|
| 9 | | | 44 |
| 10 | | | 20 |
| 11 | | | 56[b] |
| 12 | | | $R_2$ = F, 62<br>$R_2$ = Cl, 63<br>$R_2$ = OCH$_3$, 80 |

[a]Temperature controlled at −78° C. to 23° C.
[b]Temperature was held constant at −10° C.

In order that the embodiments of the invention may be more readily understood, reference is made to the following example which is intended to illustrate the embodiments of the invention, but not limit to the scope thereof.

Example 1

1 mmol of an oxime reaction product (formed from heating 1-(2-aminophenyl)ethanone, hydroxylamine (supplied as hydroxylamine hydrochloride), and sodium hydroxide at 60°) was dissolved in dichloromethane (15 mL), and 2 mmol of triethylamine was added. The reaction was stirred at 23° for 15 minutes, then cooled to 0° C. A 5 mL solution of methanesulfonylchloride (1.2 mmol) in dichloromethane was added slowly, and the reaction was warmed to 23° C. over 5 hours. The reaction was concentrated in vacuo and purified via column chromatography. The product was isolated as a white or off-white to yellow solid or viscous oil, and the yield was about 77%.

Having described the invention in detail and by reference to preferred embodiments thereof, it will be apparent that modifications and variations are possible without departing from the scope of the invention.

What is claimed is:

1. A method for making a 1H-indazole compound comprising:

providing an aromatic carbonyl compound having the formula

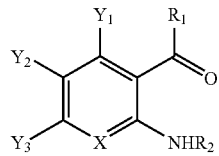

where $R_1$ is H, an alkyl, an aryl, or heteroaryl; $R_2$ is H, an alkyl, aryl, allyl, alkylsulfonyl, or arylsulfonyl; X is N or $CY_4$; $Y_1$, $Y_2$, $Y_3$, and $Y_4$ independently represent H, an alkyl, aryl, alkoxy or halogen; and wherein optionally one or more of $Y_1$ and $Y_2$, $Y_2$ and $Y_3$, or $Y_3$ and $Y_4$ can be connected to form at least one ring;

reacting said aromatic carbonyl compound with a nitrogen-containing base to form an oxime reaction product having the formula

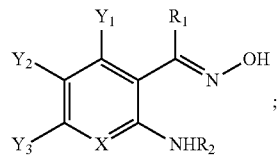

and adding an activating agent in the presence of a weak base to said oxime reaction product such that said oxime reaction product is converted to a 1H-indazole compound.

2. The method of claim 1 wherein said at least one ring is optionally substituted with one or more groups selected from alkyl, aryl, alkoxy, and halogen.

3. The method of claim 1 wherein said oxime reaction product is converted at a temperature between about 0° C. and about 23° C.

4. The method of claim 1 wherein said aromatic carbonyl compound is selected from the group consisting of o-aminobenzaldehydes and o-aminoketones.

5. The method of claim 1 wherein said nitrogen-containing base comprises hydroxylamine.

6. The method of claim 1 wherein said activating agent is selected from methanesulfonylchloride, tosyl chloride, methylchloroformate, and pentafluorobenzoyl chloride.

7. The method of claim 1 wherein said weak base is selected from triethylamine and 2-aminopyridine.

8. The method of claim 1 wherein $R_2$ is an aryl.

9. The method of claim 1 wherein $R_2$ is H.

10. The method of claim 1 wherein X is CH.

11. The method of claim 10 where $Y_1$, $Y_2$, and $Y_3$ are H.

12. The method of claim 10 where $R_2$ is an aryl.

13. The method of claim 1 wherein $Y_2$ and $Y_3$ are joined to form a 6-membered aromatic ring.

14. The method of claim 13 wherein said 6-membered aromatic ring is substituted with one or more groups selected from alkyl, aryl, alkoxy, and halogen.

15. The method of claim 1 wherein X is N.

16. The method of 15 wherein $Y_1$, $Y_2$, and $Y_3$ are H.

* * * * *